United States Patent [19]

Keives

[11] Patent Number: 4,911,026

[45] Date of Patent: Mar. 27, 1990

[54] GRAIN PROBE

[76] Inventor: George Keives, 52 Primrose Crescent, Winnipeg, Manitoba, Canada, R2V 2K9

[21] Appl. No.: 334,482

[22] Filed: Apr. 7, 1989

[30] Foreign Application Priority Data

Jul. 29, 1988 [CA] Canada .................................. 573447

[51] Int. Cl.$^4$ .............................................. G01N 1/12
[52] U.S. Cl. .................................................. 73/864.64
[58] Field of Search ............ 73/864.51, 864.63, 864.64

[56] References Cited

U.S. PATENT DOCUMENTS

| | | | |
|---|---|---|---|
| 3,065,637 | 11/1962 | Landes | 73/864.64 |
| 3,109,307 | 11/1963 | Papworth | 73/864.64 |
| 3,192,773 | 7/1965 | Wilson | 73/864.64 |
| 4,179,930 | 12/1979 | Chrisp | 73/864.64 |
| 4,359,110 | 11/1982 | Peterson | 73/864.64 |
| 4,790,198 | 12/1988 | Awtry et al. | 73/864.64 |
| 4,800,765 | 1/1989 | Nelson | 73/864.64 |

*Primary Examiner*—Robert R. Raevis
*Attorney, Agent, or Firm*—Murray E. Thrift; Stanley G. Ade; Adrian D. Battison

[57] ABSTRACT

A grain probe consists of an elongate hollow tube. The tube has a solid nose with a tapered end and a helical rib on its outside surface. The rib has a short radial extent, considerably less than the diameter of the tube. Immediately following the helical rib is a sampling valve with a sample opening in the side wall of the tube. This is covered by a valve sleeve that slides between a closed position covering the opening and an open position engaging the end of the helical rib. The valve is retained in the closed position by a cut-out in the end of the sleeve engaging over a stud projecting from the wall of the tube. The cut-out is L-shaped and oriented so that rotation of the tube to drive it into grain will keep the stud engaged in the cut-out. The valve sleeve may carry ribs projecting into the surrounding grain to ensure that when the cut-out and stud are disengaged, the sleeve will remain stationary in the grain while the tube moves to open the sample opening. The tube is segmented to provide for ease in handling when not in use and also to enable the tube to be varied in length.

13 Claims, 2 Drawing Sheets

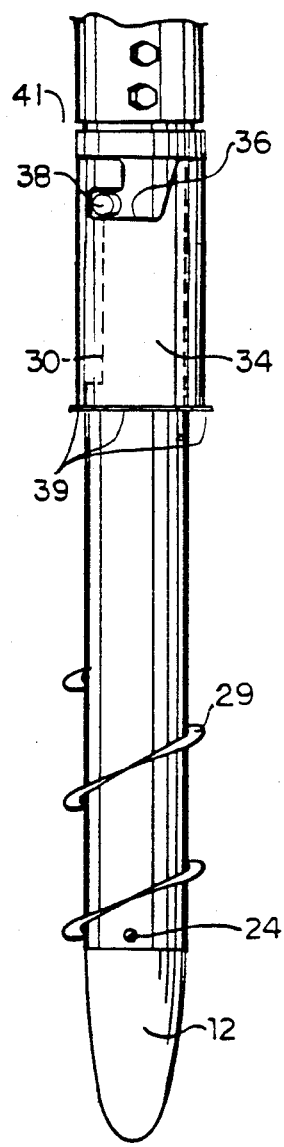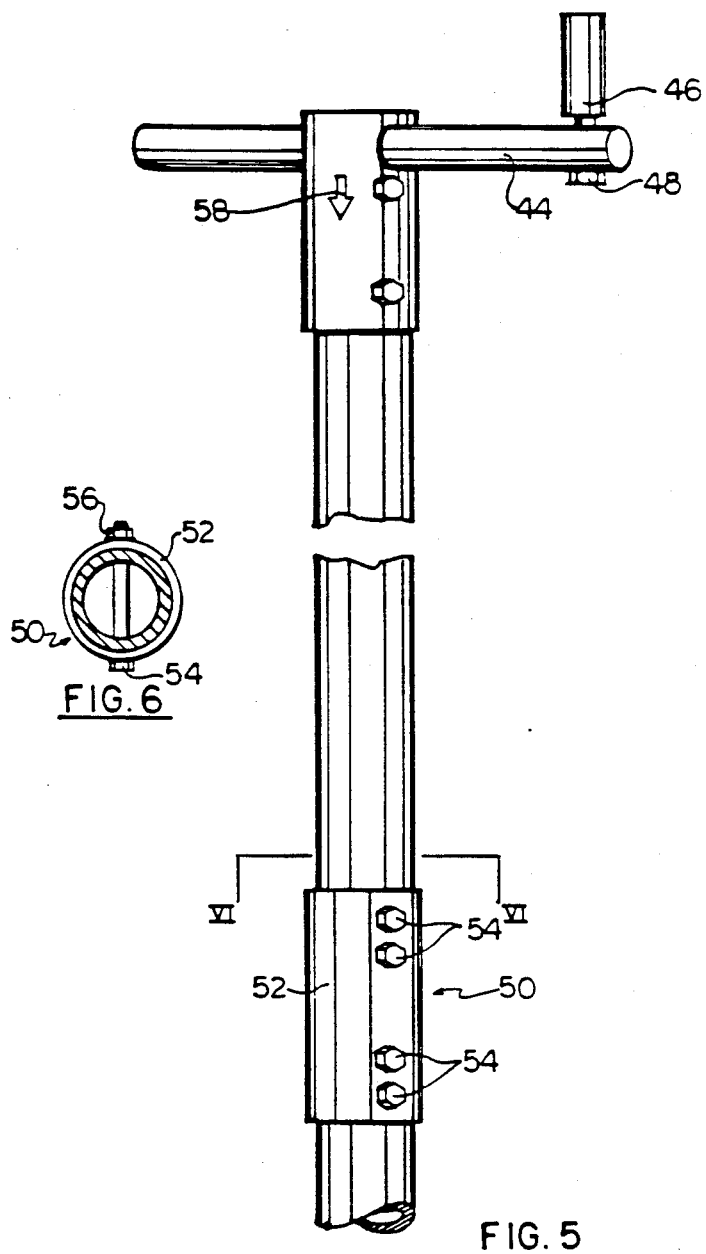

GRAIN PROBE

FIELD OF THE INVENTION

The present invention relates to grain probes and more particularly to elongate probes used in obtaining samples of grain at selected depths in storage bins or the like.

BACKGROUND

One form of known grain probe is a hollow tube with a closed nose end and a valve in the tube spaced from the nose. A probe of this sort is inserted into the grain to the depth desired, the valve is opened to allow a sample of grain to enter the tube and then the tube is withdrawn along with the sample. The sample may be poured out of the upper end of the tube for subsequent testing. Known probes of this sort suffer from a number of disadvantages, including difficult insertion and/or withdrawal of the probe, unreliable valve operation and unwieldy dimensions.

The present invention proposes certain improvements in grain probes of this sort.

SUMMARY

According to the present invention there is provided a grain probe comprising:
- an elongate hollow tube;
- a closed, tapered nose on one end of the hollow tube;
- a helical rib on the outside surface of the tube such that on rotation of the tube in a first direction, the rib acts as a screw to advance the tube into a body of grain;
- a sample opening in the tube spaced from the nose;
- a valve for selectively closing and opening the sample opening, comprising a sleeve mounted slideably on the tube between a closed position extending over the sample opening and an open position located between the sample opening and the nose of the tube; and
- latch means for normally retaining the sleeve in the closed position and releasing said sleeve for free sliding movement on the tube in response to rotation of the tube relative to the sleeve in the direction opposite to said first direction.

The rotation responsive latch for the valve sleeve may be a cut-out at the end of the sleeve engaging over a stud projecting from the wall of the tube. During insertion the tube is rotated in the one direction, usually clockwise. This causes the rib to draw the tube into the grain and retains the valve sleeve in the closed position. A short, opposite rotation of the tube frees the valve sleeve because the friction between the surrounding grain and the sleeve inhibits rotation of the sleeve. The tube may then be pulled out of the grain slightly to uncover the sample opening.

In preferred embodiments of the invention, the rib is very shallow, to present as little resistance as possible to both insertion and withdrawal.

Where the grain pressure on the sleeve is insufficient to inhibit its movement during valve opening, the sleeve may be provided with shallow ribs to provide the necessary force retarding the rotation of the sleeve.

A collar may be fixed to the tube to engage the outer end of the sleeve in the closed position. This inhibits binding of the latch stud in the cut-out.

The tube is preferably made from a number of tubular segments joined end to end. The tubes are desirably joined by coupling sleeves extending over adjacent ends of the tube segments and bolted to them by bolts arranged along a common line axially of the tube and at right angles to the sample opening. A coupling of this sort provides a smooth internal surface on the side of the tube opposite the sample opening, allowing the grain to be poured out easily.

It is also preferred to provide an indicator mark on the outer end of the tube to indicate the location of the sample opening around the tube so that when the valve is to be opened or grain poured from the tube, the tube can be turned to bring the sample opening to the top.

BRIEF DESCRIPTION OF THE DRAWINGS

In the accompanying drawings, which illustrate an exemplary embodiment of the present invention:

FIG. 4 illustrates the sampling section of FIG. 2 with the valve closed;

FIG. 5 illustrates the outer end section of the tube along with a tube section coupling; and FIG. 6 is a view along line VI—VI of FIG. 4.

DETAILED DESCRIPTION

Figure 1:
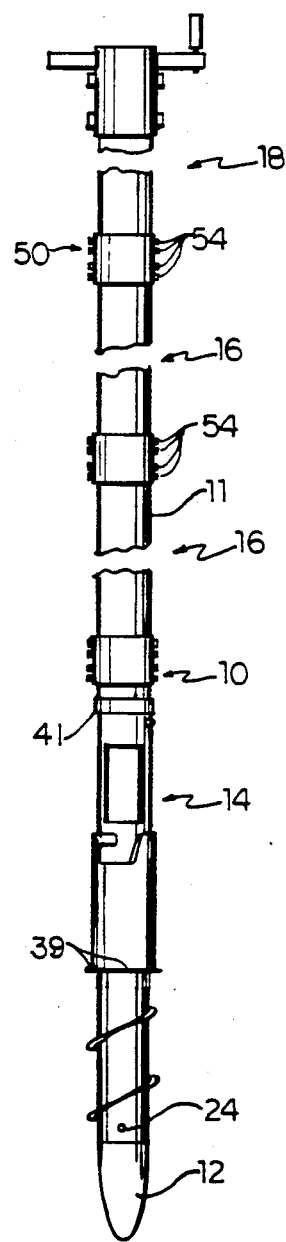
FIG. 1 illustrates a grain probe according to the present invention.

Referring to the drawings, and especially to FIG. 1, there is illustrated a grain probe 10 consisting of an elongate hollow tube 11 with a closed, tapered nose 12. The tube includes a sampling section 14 to which the nose 12 is connected, two intermediate tube sections 16 connected between the sampling section and an outer end section 18. The length of the tube can be varied by removing one or both of the intermediate sections or installing additional intermediate sections as desired.

Figure 2:
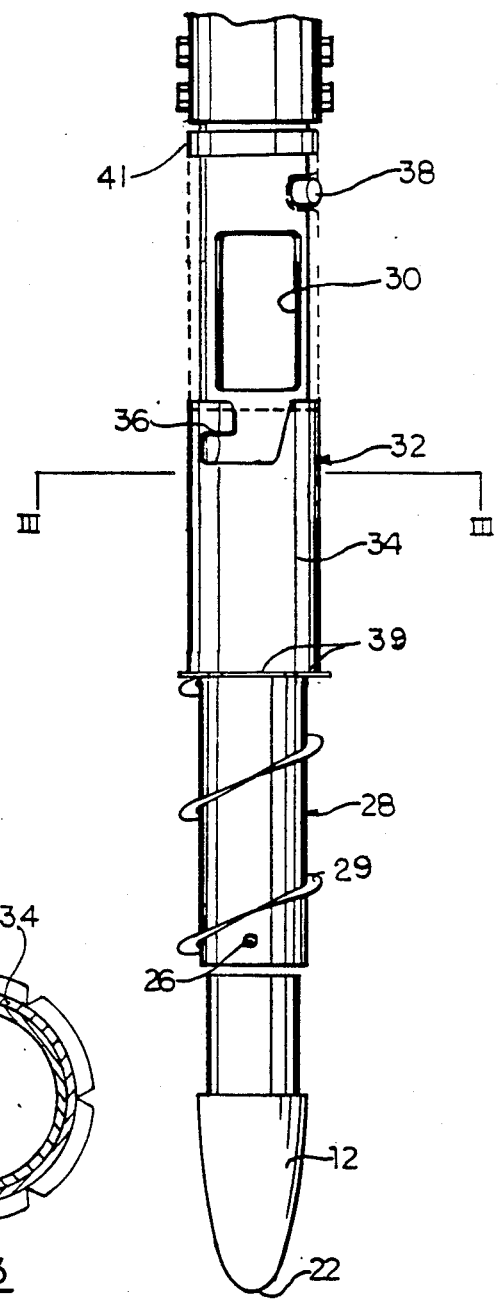
FIG. 2 illustrates a leading end section of the grain probe including a sampling section.

As illustrated most particularly in FIG. 2, the nose 12 consists of a solid block of lightweight material, for example aluminum, plastics material or wood with a leading tapered end 22. The opposite end is cylindrical and fits snugly into the open leading end of the tube 11. Three screws 24 evenly spaced around the tube pass through holes 26 in the tube to secure the nose in place.

The section 28 of the tube 11 adjacent the nose 12 carries a helical rib 29 that projects from the side wall of the tube. The radial extent of the rib is very small compared to the diameter of the tube. This section 28 of tube 11 constitutes the sampling section of the probe. A sample opening 30 is formed in the side wall of the tube section 28 at a position spaced from the rib 29.

A valve 32 for the sample opening 30 consists of a sleeve 34 that slides on the sampling section tube 28 between the open position illustrated in solid line in FIG. 2 and a closed position illustrated in broken line. An L-shaped cut-out 36 is formed in the trailing end of the sleeve 34 to engage a radially projecting stud 38 on the side wall of the sampling section tube when the sleeve is in the closed position, covering the sample opening 30. The undercut end of the cut-out is directed in the direction of rotation that causes the helical rib 24 on the nose section to draw the tube into a body of grain. In most cases this is a right hand, clockwise rotation, so that the undercut projects clockwise when seen from the outer end of the probe. When the stud 38 is disengaged from the cut-out 36, the sleeve is free to slide along the sampling tube to engage the end of the rib 24, which acts as a stop. This movement uncovers the sample opening 30. The sliding movement of the sleeve 34 is assisted by the short circumferential ribs 39 on the sleeve, projecting into the grain. These ribs 39 are formed by radially cutting the end of the sleeve 34 adjacent the rib 24, and bending the resulting segments outward. The ribs 39 also serve to retard rotation of the sleeve 34 in a body of grain when the tube 11 is rotated to disengage the stud 38 from the cut-out 36.

Above the stud 38, the tube section 28 carries a fixed collar 41 that engages the end of the sleeve 34 in the closed position so that stud 38 is central in the cut-out 36 and does not cause binding of the sleeve in the closed condition. The collar also prevents cracked grain and weed seeds from slipping between the sleeve and the tube, to prevent binding.

Each intermediate section 16 of the tube is a plain tube coupled at its opposite ends to the adjacent tube sections.

The outer end section of the probe tube 11 is a hollow tube like the sampling section. At its outer end however, it carries a diametrically arranged bar 44 with a handle 46 mounted on one of its ends with a bolt 48. The bar 44 thus acts as handle for the probe, while the handle 46 serves a crank for turning the probe into a body of grain.

Apart from the coupling between the nose 12 and the leading end of the tube 11, the tube sections are joined by couplings such as coupling 50 illustrated in FIGS. 5 and 6. The coupling consists of a coupling sleeve 52 that extends over the adjacent ends of two tube sections butted end to end. The sleeve is connected to each tube section by two bolts 54 held in place by respective nuts 56. The bolts are fitted through aligned bores in the sleeve and the tube section. The multiple bolts ensure that even if one fastener does come loose, the tube 11 remains intact. The bolts of all of the couplings are aligned in a single axial plane, transverse to the sample opening 30 as illustrated most particularly in FIG. 1. This ensures that on the side of the tube opposite the sample opening, the inside is completely smooth so that grain can be poured out without becoming lodged in or against irregularities on the inner surface. The bar 44 is aligned in the same plane as the bolts.

At the upper end of the outer section 18, the tube 11 carries an indicator mark 58 to show the location of the sample opening 30 around the tube. This allows the operator of the probe to position the sample opening as desired when the probe is in use.

Figure 3:
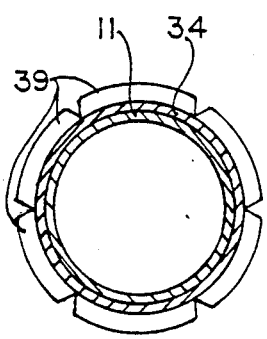
FIG. 3 is a view along line III—III of FIG. 2.

To use the probe, the sleeve 34 is first locked in the closed position. The probe is then pushed as far as possible into the grain. The crank is then used to screw the probe into the desired depth. The clockwise rotation of the tube maintains the stud 38 in the cut-out 36, which in turn retains the sleeve 34 in the closed position illustrated in FIG. 3. Once the sample opening 30 has reached the desired depth, the tube 11 is rotated counter clockwise slightly to disengage the stud 38 from the cut-out 36. A small upwards pull then brings the sleeve 34 to its open position, leaving the sample opening open. A slight additional movement of the tube will fill the sample chamber of the tube. The tube is then drawn out of the grain. It is recommended that the sleeve 34 be locked on the stud 38, and then grain can be poured from the open end of the tube 11 into an appropriate container.

The probe of the present invention may be used to sample grain at both the upper levels in a bin and the lower levels, by using the grain auger port for access.

While one embodiment of the invention has been described in the foregoing, it is to be understood that other embodiments are possible. The scope of the invention is to be determined solely by reference to the accompanying claims.

I claim:

1. A grain probe comprising:
   an elongate hollow tube;
   a closed, tapered nose on one end of the hollow tube;
   a helical rib on the outside surface of the tube such that on rotation of the tube in a first direction, the rib acts as a screw to advance the tube into a body of grain;
   a sample opening in the tube spaced from the nose;
   a valve for selectively closing and opening the sample opening, comprising a sleeve mounted slideably on the tube between a closed position extending over the sample opening and an open position located between the sample opening and the nose of the tube;
   a collar mounted on the tube and engaging an end of the sleeve facing away from the nose in the closed position of the sleeve; and
   latch means for normally retaining the sleeve in the closed position and releasing said sleeve for free sliding movement on the tube in response to rotation of the tube relative to the sleeve in the direction opposite to said first direction.

2. A probe according to claim 1 wherein the helical rib has a depth radially of the tube substantially less than the diameter of the tube.

3. A probe according to claim 1 wherein the latch means comprise an L-shaped cut-out in the end of the sleeve remote from the nose section and a stud on the tube loosely engagable in the cut-out.

4. A probe according to claim 3 including movement retarding means on the sleeve.

5. A probe according to claim 4 wherein the movement retarding means comprise rib means on the sleeve.

6. A probe according to claim 5 wherein the rub means comprise a plurality of ribs on the sleeve.

7. A probe according to claim 6 wherein the ribs are circumferentially oriented.

8. A probe according to claim 1 wherein the hollow tube comprises a plurality of tube segments joined end to end.

9. A probe according to claim 8 including coupling means for joining adjacent ends of adjacent tube segments.

10. A probe according to claim 9 wherein each coupling means comprises a coupling sleeve extending over the adjacent ends of the adjacent tube segments and fastener means securing the coupling sleeve to each of the adjacent tube segments.

11. A probe according to claim 10 wherein the fastener means comprise bolts.

12. A probe according to claim 11 wherein the bolts are aligned in a single axial plane along the tube.

13. A probe according to claim 1 including indicator means on an end of the tube remote from the nose positioned to indicate the location of the sample opening around the tube.

* * * * *